United States Patent [19]

Burri

[11] 4,154,463
[45] May 15, 1979

[54] PRESSURE-SENSITIVE OR HEAT-SENSITIVE RECORDING MATERIAL CONTAINING A CARBAZOLYL METHANE COMPOUND

[75] Inventor: Peter Burri, Reinach, Switzerland

[73] Assignee: Ciba-Geigy Corporation, Ardsley, N.Y.

[21] Appl. No.: 842,854

[22] Filed: Oct. 17, 1977

[30] Foreign Application Priority Data

Oct. 26, 1976 [LU] Luxembourg .................... 76074

[51] Int. Cl.² ................. B41M 5/16; B41M 5/18; B41M 5/22
[52] U.S. Cl. .................... 282/27.5; 106/21; 260/315; 427/151; 428/307; 428/913; 428/914
[58] Field of Search ............... 282/27.5; 427/150, 151; 428/307, 323, 411, 537, 913, 914; 106/21; 260/315

[56] References Cited

U.S. PATENT DOCUMENTS

| | | | |
|---|---|---|---|
| 3,957,288 | 5/1976 | Lemahieu et al. | 282/27.5 |
| 3,958,815 | 5/1976 | Poot et al. | 282/27.5 |
| 3,995,088 | 11/1976 | Garner et al. | 428/323 |
| 4,054,718 | 10/1977 | Garner et al. | 428/454 |

Primary Examiner—George F. Lesmes
Assistant Examiner—Bruce H. Hess
Attorney, Agent, or Firm—Prabodh I. Almaula

[57] ABSTRACT

The present invention provides a pressure- or heat-sensitive recording material which contains in its color forming system at least one carbazolylmethane compound of the formula

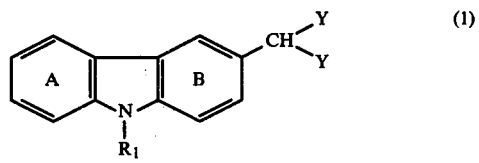

wherein Y is an amino-substituted phenyl radical of the formula

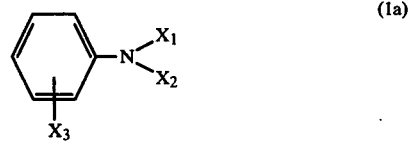

or an indolyl radical of the formula

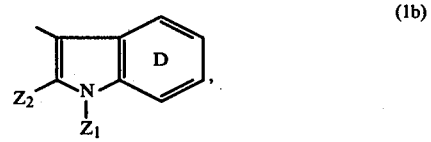

in which formulae each of $X_1$ and $X_2$ is hydrogen, alkyl of at most 12 carbon atoms which is unsubstituted or substituted, cycloalkyl, phenyl, benzyl, substituted phenyl or substituted benzyl, or $X_1$ and $X_2$ together with the nitrogen atom to which they are attached represent a 5- or 6-membered, heterocyclic radical, $X_3$ is hydrogen, halogen, nitro, lower alkyl or lower alkoxy, each of $R_1$ and $Z_1$ is hydrogen, alkyl of not more than 12 carbon atoms which is unsubstituted or substituted; acyl of 1 to 12 carbon atoms, phenyl, benzyl, substituted phenyl or substituted benzyl, and $Z_2$ is hydrogen, lower alkyl or phenyl, and the rings A, B and D independently can be further substituted. This material yields copies of improved color intensity and lightfastness.

10 Claims, No Drawings

PRESSURE-SENSITIVE OR HEAT-SENSITIVE RECORDING MATERIAL CONTAINING A CARBAZOLYL METHANE COMPOUND

The present invention relates to a pressure-sensitive or heat-sensitive recording material which contains as colour former in its colour forming system at least one carbazolylmethane compound of the general formula

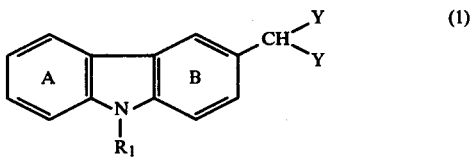     (1)

wherein
Y represents an amino-substituted phenyl radical of the formula

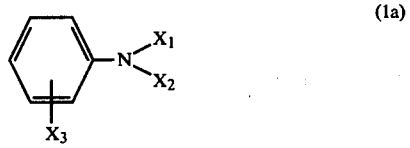     (1a)

or an indolyl radical of the formula

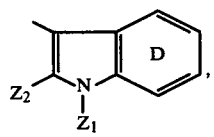     (1b)

in which formulae each of
$X_1$ $X_2$ independently represents hydrogen, alkyl of at most 12 carbon atoms which is unsubstituted or substituted by halogen, hydroxyl, cyano or lower alkoxy; cycloalkyl, phenyl, benzyl, or phenyl or benzyl which is substituted by halogen, lower alkyl or lower alkoxy, or $X_1$ and $X_2$ together with the nitrogen atom to which they are attached represent a 5- or 6-membered, preferably saturated, heterocyclic radical, $X_3$ represents hydrogen, halogen, nitro, lower alkyl or lower alkoxy, each of $R_1$ and $Z_1$ independently represents hydrogen, alkyl of not more than 12 carbon atoms which is unsubstituted or substituted by halogen, hydroxyl, cyano or lower alkoxy; acyl of 1 to 12 carbon atoms, phenyl, benzyl, or phenyl or benzyl which is substituted by halogen, lower alkyl, lower alkoxy or nitro, and $Z_2$ represents hydrogen, lower alkyl or phenyl, and the rings A, B and D independently can be further substituted by cyano, nitro, halogen, lower alkyl, lower alkoxy or lower alkylcarbonyl.

By lower alkyl and lower alkoxy in the definition of the radicals of the carbazolylmethane compounds are usually meant those groups and group components which contain from 1 to 5, in particular 1 to 3, carbon atoms. Lower alkyl is for example methyl, ethyl, n-propyl, isopropyl, n-butyl, sec-butyl or amyl, and lower alkoxy is for example methoxy, ethoxy or isopropoxy. Halogen in connection with all the above substituents is for example fluorine, bromine or preferably chlorine.

Alkyl radicals represented by $X_1$, $X_2$, $R_1$ and $Z_1$ can be straight-chain or branched. Examples of such alkyl radicals are: methyl, ethyl, n-propyl, isopropyl, n-butyl, sec-butyl, n-hexyl, n-octyl or n-dodecyl.

Substituted alkyl radicals represented by $X_1$, $X_2$, $R_1$ and $Z_1$ are in particular cyanoalkyl, haloalkyl, hydroxyalkyl, alkoxyalkyl, each containing 2 to 4 carbon atoms, for example β-cyanoethyl, β-chloroethyl, β-hydroxyethyl, β-methoxyethyl or β-ethoxyethyl.

Cycloalkyl represented by $X_1$ and $X_2$ is for example cyclopentyl or preferably cyclohexyl.

Preferred substituents in the benzyl and phenyl group of the radicals X, $Z_1$ and $R_1$ are for example halogen atoms, methyl or methoxy groups. Examples of such araliphatic and aromatic radicals are: p-methylbenzyl, o- or p-chlorobenzyl, o- or p-tolyl, xylyl, o-, m- or p-chlorophenyl or o- or p-methoxyphenyl.

A heterocyclic radical represented by $X_1$ and $X_2$ together with the nitrogen atom to which they are attached is for example pyrrolidino, piperidino, pipecolino, morpholino, thiomorpholino or piperazino.

Alkenyl represented by $R_1$ and $Z_1$ is for example allyl, 2-methallyl, 2-ethallyl, 2-butenyl or octenyl.

An acyl radical within the definition of $R_1$ and $Z_1$ is in particular lower alkylcarbonyl, for example formyl, acetyl or propionyl, or benzoyl. Benzoyl can be substituted in the benzene ring by halogen, methyl or methoxy.

Each of $X_1$, $X_2$, $Y_2$ and $Z_1$ independently represents preferably lower alkyl or benzyl, whilst $Z_2$ preferably represents methyl or phenyl. Advantageously, $X_1$ and $X_2$ can also represent phenyl or lower alkoxyphenyl. $X_3$ preferably represents hydrogen, methyl, methoxy or chlorine. $R_1$ is preferably alkyl of 1 to 8 carbon atoms or benzyl and, in particular, ethyl, n-butyl or n-octyl.

The rings A, B and D are preferably not further substituted, but if they do contain substituents, each independently is further substituted in particular by halogen, lower alkyl or lower alkoxy, for example by chlorine, methyl or methoxy. Each benzene ring can advantageously contain 1 or 2 substituents. The substituents of the rings A and D are preferably in the para-position to the nitrogen atom.

Carbazolylmethane compounds which are of practical importance have the general formula

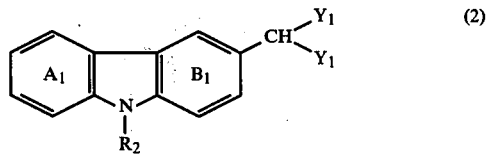     (2)

wherein
$Y_1$ represents an amino-substituted phenyl radical of the formula

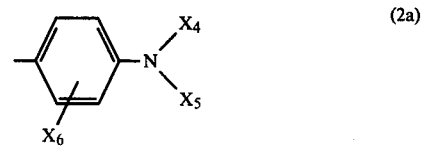     (2a)

or an indolyl radical of the formula

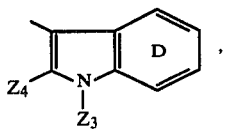

in which formulae each of

X$_4$ and X$_5$ independently represents lower alkyl, phenyl, lower alkoxyphenyl or benzyl and X$_4$ also represents hydrogen, or X$_4$ and X$_5$ together with the nitrogen atom to which they are attached represent pyrrolidino, piperidino or morpholino, X$_6$ represents hydrogen, halogen, lower alkyl or lower alkoxy, each of R$_2$ and Z$_3$ independently represents hydrogen, alkyl of not more than 12 carbon atoms which is unsubstituted or substituted by halogen, cyano or lower alkoxy; phenyl; or benzyl which is unsubstituted or substituted by halogen, lower alkyl or lower alkoxy, and Z$_4$ represents hydrogen, methyl or phenyl, and each of the rings A$_1$, B$_1$ and D$_1$ independently can be further substituted by cyano, halogen, lower alkyl or lower alkoxy.

Preferred carbazolylmethane compounds of the formulae (1) and (2) above are those in which the radicals Y are amino-substituted phenyl radicals of the formula (1a) or (2a).

Particularly interesting carbazolylmethane compounds are those of the general formula (3) or (4)

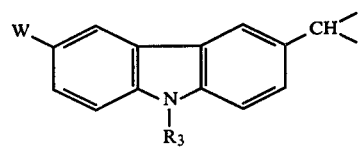

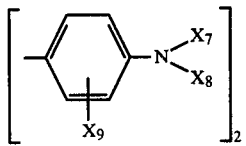

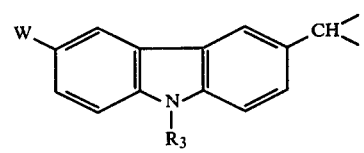

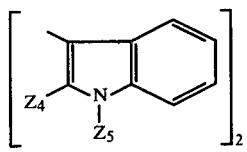

wherein

R$_3$ represents alkyl of 1 to 8 carbon atoms, phenyl or benzyl,

W represents hydrogen, halogen, nitro or methyl,

X$_7$ represents lower alkyl, phenyl, lower alkoxyphenyl or benzyl,

X$_8$ represents hydrogen, lower alkyl or benzyl,

X$_9$ represents hydrogen, methyl or methoxy,

Z$_4$ represents hydrogen, methyl or phenyl, and

Z$_5$ represents hydrogen, alkyl of 1 to 8 carbon atoms, benzyl or phenyl.

The carbazolylmethane compounds of the formula (3) are preferred.

Particularly preferred compounds of the formula (3) or (4) are those in which W is hydrogen. In this case, R$_3$ in formula (3) preferably represents alkyl of 1 to 8 carbon atoms, in particular lower alkyl, for example ethyl or n-butyl, X$_8$ represents lower alkyl, X$_7$ represents phenyl or lower alkoxyphenyl, and X$_9$ represents hydrogen or methyl, whilst in formula (4) each of R$_3$ and Z$_4$ preferably represents lower alkyl and Z$_4$ represents methyl.

The carbazolylmethane compounds of the formula (1) are obtained by reacting 1 mole of an aldehyde of the general formula

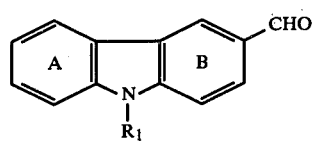

with 2 moles of a compound of the general formula (6) or (7)

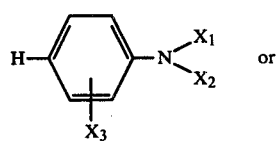

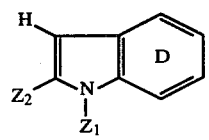

wherein A, B, D, R$_1$, X$_1$, X$_2$, X$_3$, Z$_1$ and Z$_2$ have the given meanings.

The majority of the carbazole aldehydes of the formula (5) are known, for example from J. Am. Chem. Soc. 73, 98–100 (1951). They are obtained by formylation of the corresponding carbazole compounds with dialkylformamidines in the presence of an acid halide and can also be used direct without isolation for reaction with the compounds of the formula (6) or (7).

The reaction of the compounds of the formula (5) with the compounds of the formula (6) or (7) is advantageously carried out at a temperature between 20° and 130° C., preferably between 50° and 115° C. and in the presence of sulphuric acid, preferably 70 to 98% sulphuric acid. The reaction time depends on the temperature and is usually from 1 to 8 hours. To promote the solubility of the reagents and the product, it is possible to add lower aliphatic carboxylic acids or alcohols, for example acetic acid or isopropyl alcohol, to the reaction mixture, in which case the reaction temperature is between 20° C. and the reflux temperature of the mixture. In some cases it is advantageous to add urea in order to shorten the reaction time and to increase the yield. Instead of sulphuric acid, it is possible to use hydrochloric acid, zinc chloride, iron(III) chloride, aluminium chloride, polyphosphoric acid, phosphoroxy chloride, thionyl chloride or phosphorus pentoxide. It is often advantageous to use acetic anhydride both as reagent and as solvent. In this case, if for example y represents an unsubstituted indolyl or carbazolyl radical at the nitrogen atom, an acetyl group can be introduced at the nitrogen atom during the reaction. The reaction can also be carried out in a water-insoluble solvent using for example phosphoroxy chloride or catalytic amounts of an organic sulphonic acid, for example p-toluenesulphonic acid.

The isolation of the end product of the formula (1) is effected in a manner which is known per se, for example by pouring the reaction mixture into ice-water, if appropriate while neutralising the acid with an alkaline compound, for example ammonia, an alkali metal hydroxide or an alkali metal carbonate, collecting the precipitate by filtration or evaporating off the water-insoluble solvent, and by washing and drying the product, as well as, is appropriate, by chromatography or recrystallisation of the product, which in certain cases can contain insignificant amounts of polycondensation products.

The carbazolylmethane compounds of the formulae (1) to (4) are normaly colourless or faintly coloured. When these colour formers are brought into contact with an acid developer, i.e. an electron acceptor, they produce intense orange, red, violet and green shades of excellent lightfastness, depending on the meaning of Y. They are therefore also very useful when mixed with other known colour formers, for example 3,3-(bis-aminophenyl)-phthalides 3,3-(bis-indolyl)-phthalides, 2,6-diaminofluoranes or spiropyranes, in order to give blue, navy blue, grey or black colourations.

The carbazolylmethane compounds of the formula (1) to (4) exhibit both on clay and on phenolic substrates an improved colour intensity and lightfastness. They are suitable in particular as slowly developing colour formers for use in a pressure-sensitive recording material, which can also be a copying material.

A pressure-sensitive material comprises for example at least one pair of sheets, which contain at least one colour former of the formulae (1) to (4) dissolved in an organic solvent and an electron acceptor substance as developer. The colour former effects a coloured marking at those points where it comes into contact with the electron acceptor substance.

Typical examples of such developers are attapulgite clay, silton clay, silica, bentonite, halloysite, aluminium oxide, aluminium sulphate, aluminium phosphate, zinc chloride, kaolin or any clay or organic compounds with acid reaction, for example unsubstituted or ring-substituted phenols, salicylic acid or esters of salicyclic acid and the metal salts thereof, or an acid polymeric material, for example a phenolic polymer, an alkylphenolacetylene ring, a maleic acid/rosin resin or a partially or completely hydrolysed polymer of maleic acid and styrene, ethylene, vinyl methyl ether or carboxypolymethylene. Preferred developers are attapulgite clay, silton clay or phenolformaldehyde resin. According to the invention, these developers and, in particular, attapulgite clay and silton clay, can be applied to paper not only in the customary alkaline to neutral range, for example at pH values between 7 and 12, preferably between 8 and 10, but also in the acid range, for example at pH values between 3 and 6.9 preferably between 4 and 6, whereby the carbazolylmethane compounds are distinguished in the acid range even by a higher rate and colour intensity during the colour development. These electron acceptors are preferably applied in the form of a layer to the face of the receiver sheet.

In order to prevent the colour formers contained in the pressure-sensitive recording material from becoming active too soon, they are usually separated from the electron acceptor substance. This can advantageously be accomplished by incorporating the colour formers in foam-like, sponge-like or honeycomb-like structures. Preferably, however, the colour formers are enclosed in microcapsules, which as a rule can be ruptured by pressure.

When the capsules are ruptured by pressure, for example with a pencil, and the colour former solution is transferred in this manner to an adjacent sheet which is coated with an electron acceptor, a coloured area is produced. This colour results from the dye which is formed and which is absorbed in the visible range of the electromagnetic spectrum.

The colour formers are encapsulated preferably in the form of solutions in organic solvents. Examples of suitable solvents are preferably non-volatile solvents, for example polyhalogenated diphenyl, such as trichlorophenyl or a mixture thereof with liquid paraffin; tricresyl phosphate, di-n-butyl phthalate, dioctyl phthalate, tri-chlorobenzene, nitrobenzene, trichloroethyl phosphate, petroleum ether, hydrocarbon oils, such as paraffin, alkylated derivatives of naphthalene or diphenyl, terphenyls, partially hydrogenated terphenyl, or other chlorinated or hydrogenated condensed aromatic hydrocarbons.

The capsule walls can be formed evenly around the droplets of the colour former solution by coacervation, and the encapsulating material can consist of gelatin and gum arabic, as described e.g. in U.S. Pat. No. 2,800,457. The capsules can be formed preferably also from an aminoplast or from modified aminoplasts by polycondensation, as described in British Patent Specifications Nos. 989,264, 1,156,725, 1,301,052 and 1,355,124.

The microcapsules containing the colour formers of formula (1) can be used for the manufacture of a wide variety of known kinds of pressure-sensitive copying material. The various systems differ substantially from one another in the arrangement of the capsules, the colour reactants and the carrier material.

A preferred arrangement is that in which the encapsulated colour former is applied as a layer to the back of a transfer sheet and the electron acceptor substance as a layer to the face of a receiving sheet. However the components can also be used in the paper pulp.

Another arrangement of the constituents consists in the microcapsules which contain the colour former, and the developer, being in or on the same sheet in the form of one or more individual sheets or being present in the paper pulp.

Such pressure-sensitive copying materials are described, for example, in U.S. Pat. Nos. 2,730,457, 2,932,582, 3,418,250, 3,418,656, 3,427,180 and 3,516,846. Further systems are described in British patent specifications Nos. 1,042,596, 1,042,597, 1,042,598, 1,042,599 and 1,053,935. Microcapsules which contain the colour formers of formula (1) are suitable for each of these systems and for other pressure-sensitive systems.

The capsules are preferably secured to the carrier by means of a suitable adhesive. Since paper is the preferred carrier material, these adhesives are principally paper coating agents, for example gum arabic, polyvinyl alcohol, hydroxymethyl cellulose, casein, methyl cellulose or dextrin.

The term "paper" used herein comprises not only normal paper made from cellulose fibres, but also paper in which the cellulose fibres are replaced (partially or completely) by synthetic polymer fibres.

The carbazolylmethane compounds of the formulae (1) to (4) can also be used as colour formers in a thermoreactive recording material. This recording material contains normally at least one carrier, one colour former one electron acceptor substance and optionally one binder. Thermoreactive recording systems comprise heat sensitive recording and copying materials and papers. These systems are used, for example, for recording information, e.g. in electronic computers, teleprinters or telewriters, and in measuring instruments. The image (mark) formation can also be effected manually with a heated pen. Laser beams can also be used to produce heat-induced marks. The thermo-reactive recording material can be so composed that the colour former is dispersed or dissolved in one binder layer and the developer is dissolved or dispersed in the binder in a second layer. A second possibility consists in dispersing both the colour former and the developer in the binder in one layer. By means of heat the binder is softened at specific areas and the colour former comes into contact with the electron acceptor substance at those points where heat is applied and the desired colour develops at once.

The developers are the same electron-accepting substances as are used in pressure-sensitive papers.

Examples of developers are the clays and phenolic resins alredy mentioned, or phenolic compounds, for example 4-tert. butylphenol, 4-phenylphenol, 4-hydroxydiphenyl oxide, α-naphthol, β-naphthol, 4-hydroxymethyl benzoate, 4-hydroxyacetophenone, 2,2′-dihydroxydiphenyl, 4,4-isopropylidenediphenol, 4,4′-isopropylidene-bis-(2-methylphenol), 4,4′bis-(hydroxyphenyl)valeric acid, hydroquinone, pyrogallol, phloroglucinol, p-, m- and o-hydroxybenzoic acid, gallic acid, 1-hydroxy-2-naphthoic acid, as well as boric acid and aliphatic dicarboxylic acids, for example tartaric acid, oxalic acid, maleic acid, citric acid, citraconic acid or succinic acid.

Fusible, film-forming binders are preferably used for the manufacture of the thermoreactive recording material. These binders are normally water-soluble, whereas the colour formers and the developer are insoluble in water. The binder should be able to disperse and fix the colour former and the developer at room temperature.

By applying heat the binder softens or melts, so that the colour former comes in contact with the developer and a colour is able to form. Examples of binders which are soluble or at least swellable in water are hydrophilic polymers, for example polyvinyl alcohol, polyacrylic acid, hydroxyethyl cellulose, methyl cellulose, carboxymethyl cellulose, polyacrylic amide, polyvinyl pyrrolidone, gelatin and starch.

If the colour former and the developer are in two separate layers, it is possible to use water-insoluble binders, i.e. binders which are soluble in non-polar or only weakly polar solvents, for example natural rubber, synthetic rubber, chlorinated rubber, alkyl resins, polystyrene, styrene/butadiene copolymers, polymethylmethacrylates, ethyl cellulose, nitrocellulose and polyvinyl carbazole. The preferred arrangement, however, is that in which the colour former and the developer are contained in one layer in a water-soluble binder.

The thermoreactive coatings can contain further additives. To improve the degree of whiteness, to facilitate the printing of papers, and to prevent the heated pen from sticking, the coatings can contain, for example, talc, $TiO_2$, ZnO or $CaCO_3$ or also organic pigments, for example urea/formaldehyde polymers. In order to effect the colour formation only within a limited temperature range, it is possible to add substances such as urea, thiourea, acetanilide, phthalic anhydride or other appropriate fusible products which induce the simultaneous melting of the colour former and developer.

In the following Manufacturing Directions and Examples the percentages are by weight unless otherwise indicated.

MANUFACTURING DIRECTIONS

A. To a solution of 15 ml of glacial acetic acid, 3.8 ml of water and 2.9 g of urea are added 10.4 g of N,N-dimethylaniline and 10g of N-ethylcarbazole aldehyde. The reaction mixture is heated to 60°–70° C. and kept for 5 hours at this temperature. After cooling, the product is precipitated by the addition of 20 ml of methanol. Recrystallisation from acetone/methanol yields 7.1 g of a compound of the formula

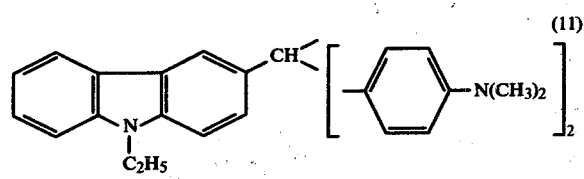

as colourless crystals with a melting point of 160°–161° C. On silton clay this colour former slowly develops an intense lightfast blue colour with λ max. at 610 nm and 515 nm.

B. The procedure of A. is repeated, substituting 11.6 g of N,N-dimethyl-m-toluidine for N,N-dimethylaniline, affording 15.2 g of a compound of the formula

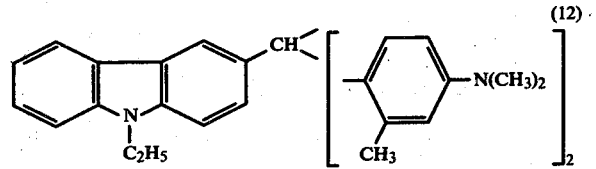

as colourless crystals which melt at 268°–271° C. On silton clay this colour former slowly develops an intense lightfast blue colour with λ max. at 610 nm.

C. 6.7 g of N-ethylcarbazole aldehyde and 12.2 g of N-phenyl-N-methyl-aminobenzene are dissolved in 20 ml of isopropanol and the solution is warmed to 30° C. To this solution are added dropwise 5.9 g of 98% sulphuric acid in such a manner that the temperature does not exceed 35° C. Then 2.7 g of urea are added, the solution is heated to 75° C. and stirred for 4 hours at this temperature. After cooling, the acid reaction solution is poured into ice-water and neutralised with 10% sodium hydroxide solution. The precipitate which forms is collected by filtration and recrystallised from acetone/methanol, affording 7.9 g of a colourless compound of the formula

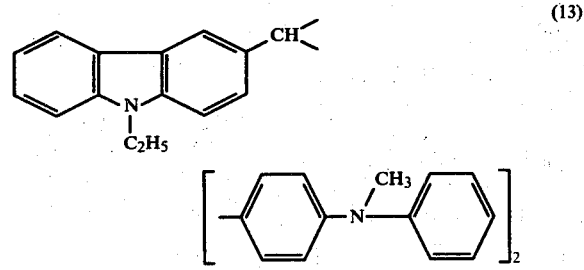

which melts at 69°–72° C. On silton clay this colour former develops an intense lightfast blue colour with λ max. at 620 nm.

D. 11.2 g of N-ethylcarbazole aldehyde and 15.9 g of 1-ethyl-2-methylindole are dissolved in 10 ml of acetic anhydride. The solution is then heated to 110° C. and kept for 4 hours at this temperature. The solution is then cooled and the product is precipitated by adding 50 ml of ethanol. The precipitate is collected by filtration and recrystallised from acetone/methanol, affording 21.3 g of a compound of the formula

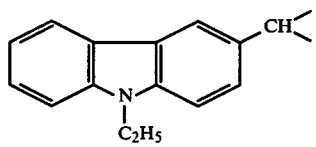

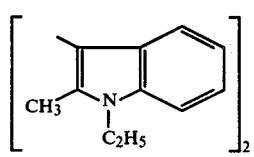

(14)

as colourless crystals which melt at 151°–154° C. On silton clay this colour former slowly develops an intense lightfast red colour with λ max. at 540 nm.

E. 4.4 g of N-ethylcarbazole aldehyde, 8.5 g of p-methoxy-N-methyl-diphenylamine and 0.7 g of urea are dissolved in 25 ml of sulpholane. To this solution are added dropwise 3.9 g of 98% sulphuric acid in such a manner that the temperature does not exceed 30° C. The reaction mixture is thereafter stirred for 5 hours at 40° C. and the resultant solution is poured into 150 ml of methanol and neutralised with 30% ammonia solution. The precipitate is collected by filtration and washed with methanol. The crude product is dissolved in methanol and freed from salt by filtration. The product is precipitated by pouring the filtrate into methanol, affording 10.4 g of a colourless compound of the formula

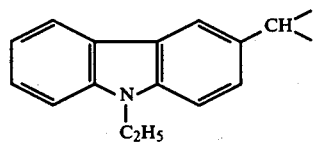

(15)

which melts at 87°–89° C. On silton clay this colour former slowly develops an intense lightfast blue colour with λ max. at 625 nm.

F. 5 g of N-butylcarbazole aldehyde and 6.5 g of N-phenylpyrrolidine are dissolved in 25 ml of ethylene chloride. To this solution are added dropwise 6.75 g of phosphoroxy chloride in such a manner that the temperature does not exceed 40° C. The reaction mixture is subsequently stirred for 5 hours under nitrogen at 60° C., then poured into water and neutralised with 30% ammonia solution. The ethylene chloride phase is separated and poured into 200 ml of methanol, whereupon the product precipitates in crystalline form. The precipitate is collected by filtration and dried to vacuo at 50° C., affording 3.1 g of a colourless compound of the formula

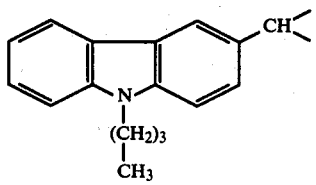

(16)

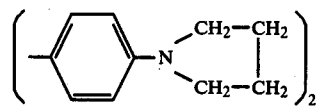

which melts at 101°–103° C. On silton clay this colour former slowly develops an intense lightfast blue colour with λ max. at 615 nm.

G. 11.1 g of N-ethylcarbazole aldehyde and 23.6 g of N-benzyl-N-methylaniline are dissolved in 70 ml of ethylene chloride. To this solution are added dropwise 18.4 g of phosphoroxy chloride in such a manner that the temperature does not exceed 40° C. The reaction mixture is then stirred for 6 hours at 70° C. under nitrogen. The reaction product is then worked up as described in F., affording 18.8 g of a colourless compound of the formula

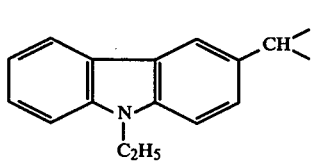

(17)

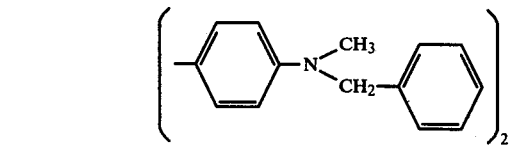

which melts at 82°–85° C. On silton clay this colour former slowly develops an intense lighfast blue colour with λ max. at 610 nm.

H. 8.55 g of N-benzylcarbazole aldehyde and 8.7 g of N,N-dimethylaniline are dissolved in 40 ml of ethylene chloride. To this solution are added 11 g of phosphoroxy chloride in such a manner that the temperature does not exceed 40° C. The reaction mixture is subsequently stirred for 5 hours at 70° C. under nitrogen and the reaction product is worked up as described in F., affording 9.5 g of a colourless compound of the formula

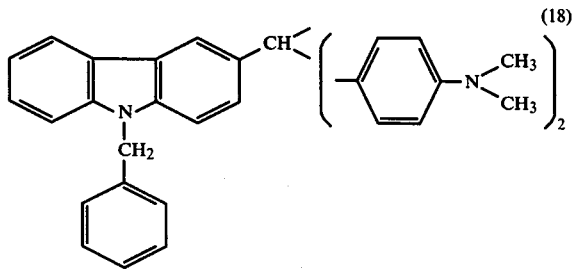

(18)

which melts at 89°–91° C. On silton clay this colour former slowly develops an intense lightfast blue colour with λ max. at 610 nm and 503 nm.

I. 7.7 g of N-n-octylcarbazole aldehyde and 7.3 g of N,N-dimethylaniline are dissolved in 30 ml of ethylene chloride. To this solution are added 9.2 g of phosphoroxy chloride and the mixture is stirred for 4 hours at 70° C. under nitrogen. The reaction product is then worked up as described in F., affording 1.6 g of a colourless compound of the formula

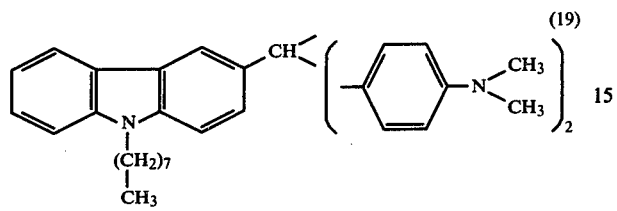

(19)

which melts at 85°–88° C. On silton clay this colour former slowly develops an intense lightfast blue colour with λ max. at 610 nm and 530 nm.n J. 5 g of N-n-butylcarbazole aldehyde and 7.7 g of N-methyl-diphenylamine are dissolved in 25 ml of ethylene chloride. To this solution are added 6.1 g of phosphoroxy chloride and the mixture is stirred for 6 hours at 70° C. under nitrogen. The reaction product is then worked up as described in F., affording 7.6 g of a colourless compound of the formula

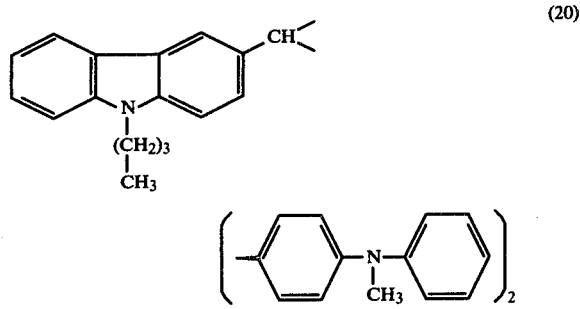

(20)

which melts at 89°–92° C. On silton clay this colour former slowly develops an intense lightfast blue colour with λ max. at 620 nm.

K. 7.7 g of N-n-octylcarbazole aldehyde and 11 g of N-methyl-diphenylamine are dissolved in 35 ml of ethylene chloride. To this solution are added 9.2 g of phosphoroxy chloride and the mixture is stirred for 3 hours at 65°–70° C. under nitrogen. The reaction product is thereafter worked up as described in F., affording 8.2 g of a colourless compound of the formula

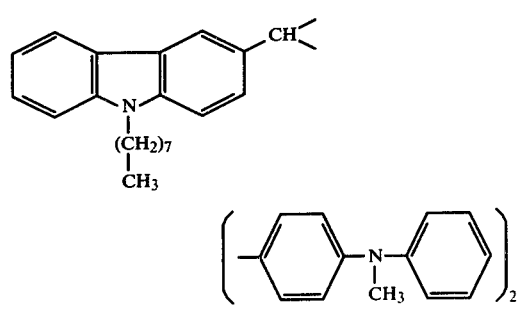

(21)

which melts at 84°–87° C. On silton clay this colour former slowly develops an intense lightfast blue colour with λ max. at 620 nm.

L. 11.1 g of N-ethylcarbazole aldehyde, 15.1 g of 3-dimethylamino-anisole and 5 g of urea are suspended in 15 ml of isopropanol. To this suspension are added 10 ml of 98% sulphuric acid at 30°–40° C. The resultant solution is then heated to 75° C. and kept for 4 hours at this temperature. After cooling, the solution is poured into ice-water and adjusted to pH 9 with 30% sodium hydroxide solution. The precipitate which forms is collected by filtration and washed with water, methanol and acetone and then dried, affording 17.1 g of a colourless compound of the formula

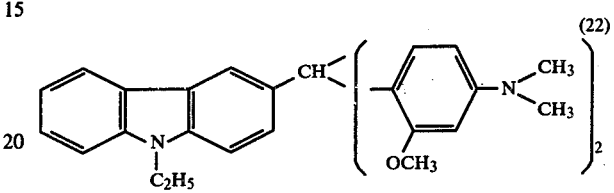

(22)

which melts at 234°–237° C. On silton clay this colour former slowly develops an intense lightfast greyish-blue colour.

M. 6.7 g of N-ethylcarbazole aldehyde and 13.2 g of 3-chloro-N,N-diethylaniline are dissolved in 70 ml of ethylene chloride. To this solution are added 11 g of phosphoroxy chloride and the reaction mixture is stirred for 10 hours at 75° C. under nitrogen. The reaction product is subsequently worked up as described in F., affording 6.9 g of a colourless compound of the formula

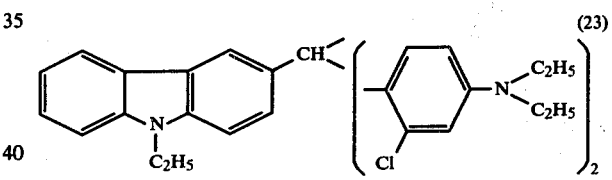

(23)

which melts at 112°–115° C. On silton clay this colour former slowly develops an intense greyish-blue colour.

N. 3.2 g of 6-chloro-N-ethyl-carbazole-3-aldehyde and 2.67 g of N,N-dimethylaniline are dissolved in 20 ml of ethylene chloride. To this solution are added 3.4 g of phosphoroxy chloride and the mixture is stirred for 5 hours at 70° C. under nitrogen. The reaction product is then worked up as described in F., affording 1.7 g of a colourless compound of the formula

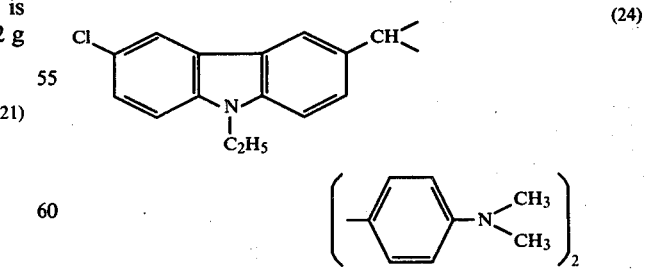

(24)

which melts at 118°–121° C. On silton clay this colour former slowly develops an intense lightfast blue colour with λ max. at 605 and 515 nm.

O. 44.6 g of N-butylcarbazole are dissolved in 23.2 g of dimethyl formamide and 50 ml of ethylene chloride.

With stirring, 46 g of phosphoroxy chloride are added to this solution in such a manner that the temperature does not exceed 30° C. The temperature is raised to 65°-70° C. in the course of 2 hours and kept thereat for 8 hours. The reaction mixture is then allowed to cool to 50° C. and 14.4 ml of water are added, whereupon the temperature rises rapidly to 70° C. The reaction solution is subsequently stirred for 30 minutes and the introduction of nitrogen is commenced.. To the solution are added 100 ml of ethylene chloride and 65.9 g of N-methyl-diphenylamine. After stirring for 16 hours at 65°-70° C. under nitrogen, the condensation is complete. After cooling, the solution is adjusted to pH 7 with 18% aqueous sodium hydroxide solution.

The organic phase is separated, washed with two 200 ml portions of water and dried over calcined sodium sulphate. To the dry ethylene chloride solution are added slowly 200 ml of acetone and the mixture is poured with stirring into 1500 ml of methanol, whereupon the product precipitates in white crystalline form. 65°-

The precipitate is collected by filtration and dried in vacuo at 50° C., affording 94.4 g of the compound of the formula (20). The melting point and the colour former properties are identical with the particulars of J.

EXAMPLE 1

Manufacture of a Pressure-sensitive Copying Paper

A solution of 3 g of the carbazolylmethane compound of formula (13) in 97g of partially hydrogenated terphenyl is emulsified in a solution of 12 g of pigskin gelatin in 88 g of water of 50° C. A solution of 12 g of gum arabic in 88 g of 50° C. is then added, followed by the addition of 200 ml of water of 50° C. The resultant emulsion is poured into 600 g of ice water and cooled until the temperature is 20° C., in the course of which the coacervation is effected. A sheet of paper is coated with the resultant suspension of microcapsules and dried. A second sheet of paper is coated with with silton clay as follows: 25 g of silton clay are suspended in 42 g of water and, with vigorous stirring, the pH is adjusted to 10 with 30% sodium hydroxide solution. After addition of 7.5 g of a binder, for example latex, the suspension is coated on paper and dried. The first sheet and the sheet of paper coated with silton clay are laid on top of each other with the coated sides face to face. Pressure is exerted on the first sheet by writing by hand or with a typewriter and an intense blue copy of excellent light-fastness slowly develops on the sheet coated with silton clay.

If the second sheet is coated with silton clay by adjusting a suspension of 25 g of silton clay and 42 g of water with 30% sodium hydroxide solution to a pH of 5, then 7.5 g of a binder are added, and the suspension is coated on paper, dried, and the procedure is repeated as described above, the colour former of the formula (13) develops its intense lightfast blue colour markedly more quickly.

EXAMPLE 2

Manufacture of a Thermoreactive Paper 6 g of an aqueous dispersion which contains 1.57% of the carbazolylmethane compound of the formula (20) and 6.7% of polyvinyl alcohol are mixed with 134 g of an aqueous dispersion which contains 14% of 4,4-isopropylidene-diphenol, 8% of attapulgite clay and 6% of polyvinyl alcohol. This mixture is applied to a paper and dried. Contacting the paper with a heated ball-point pen produces an intense blue colour of excellent lightfastness.

Intense and lightfast blue colours can also be obtained on using any of the other colour formers of the formulae (11) to (19) and (21) to (24).

I claim:

1. A pressure-sensitive or heat sensitive recording material which comprises as color formers in its color forming system at least one carbazolylmethane compound of the formula

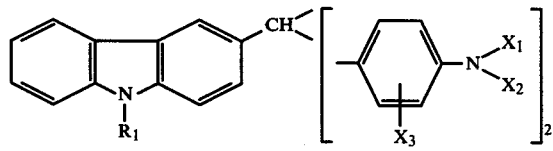

wherein $R_1$ is alkyl of 1 to 8 carbon atoms or benzyl, $x_1$ is phenyl or lower alkoxyphenyl, $x_2$ is lower alkyl and $x_3$ is hydrogen or methyl.

2. A recording material according to claim 1, wherein $R_1$ is alkyl of 1 to 8 carbon atoms.

3. A recording material according to claim 1, wherein $R_1$ is alkyl of 1 to 5 carbon atoms.

4. A recording material according to claim 1, wherein $R_1$ is ethyl, n-butyl or n-octyl.

5. A recording material to claim 1, wherein $R_1$ is ethyl, $x_1$ is phenyl, $x_2$ is methyl and $x_3$ is hydrogen.

6. A recording material according to claim 1, wherein $R_1$ is n-butyl, $x_1$ is phenyl, $x_2$ is methyl and $x_3$ is hydrogen.

7. A pressure-sensitive recording material according to claim 1 which comprises the carbazolylmethane compound dissolved in an organic solvent, and a solid electron acceptor.

8. A pressure-sensitive recording material according to claim 1 in which the carbazolylmethane compound is encapsulated in microcapsules.

9. A thermoreactive recording material according to claim 1 which comprises at least one carrier, the carbazolylmethane compound, a solid electron acceptor, and optionally a binder.

10. A process for producing a pressure-sensitive recording material which contains microcapsules containing a color former and an electron acceptor, in which the color former is a carbazolylmethane compound of the formula given in claim 1.

* * * * *